United States Patent
Yoo et al.

(10) Patent No.: US 10,597,362 B2
(45) Date of Patent: Mar. 24, 2020

(54) 3-AMINOALKYLATED INDOLE DERIVATIVE, METHOD FOR THE PREPARATION THEREOF, AND PHARMACEUTICAL COMPOSITION COMPRISING THE SAME

(71) Applicant: Seoul National University Hospital, Seoul (KR)

(72) Inventors: Ja Kyung Yoo, Gyeonggi-do (KR); Nora Lee, Gyeonggi-do (KR); Chun Ho Lee, Seoul (KR); Hyo-Soo Kim, Seoul (KR)

(73) Assignee: Seoul National University Hospital, Seoul (KR)

( * ) Notice: Subject to any disclaimer, the term of this patent is extended or adjusted under 35 U.S.C. 154(b) by 0 days.

(21) Appl. No.: 16/344,060

(22) PCT Filed: Oct. 27, 2017

(86) PCT No.: PCT/KR2017/011963
§ 371 (c)(1),
(2) Date: Apr. 23, 2019

(87) PCT Pub. No.: WO2018/080215
PCT Pub. Date: May 3, 2015

(65) Prior Publication Data
US 2019/0256465 A1 Aug. 22, 2019

(30) Foreign Application Priority Data
Oct. 28, 2016 (KR) .................. 10-2016-0141766

(51) Int. Cl.
*A61K 31/404* (2006.01)
*A61K 31/496* (2006.01)
*A61K 31/5377* (2006.01)
*C07D 403/06* (2006.01)
*C07D 413/06* (2006.01)
*A61P 9/00* (2006.01)
*A61P 9/10* (2006.01)
*A61P 9/12* (2006.01)
*C07D 209/14* (2006.01)

(52) U.S. Cl.
CPC .............. *C07D 209/14* (2013.01); *A61P 9/00* (2018.01); *A61P 9/10* (2018.01); *A61P 9/12* (2018.01)

(58) Field of Classification Search
CPC ................ A61K 31/404; A61K 31/496; A61K 31/5377; C07D 403/06; C07D 413/06; A61P 9/00; A61P 9/10; A61P 9/12
See application file for complete search history.

(56) References Cited

U.S. PATENT DOCUMENTS 4,008,085 A 2/1977 Lemahieu et al.
2003/0060497 A1 3/2003 Gerlach et al.
2015/0210672 A1 7/2015 Adams et al.

FOREIGN PATENT DOCUMENTS

WO WO-2016/029310 A1 3/2016

OTHER PUBLICATIONS

CID 72710462 (RN 1538579-66-6) Entered STN: Jan. 30, 2014.*
Lee et al., "Adenylyl Cyclase-Associated Protein 1 is a Receptor for Human Resistin and Mediates Inflammatory Actions of Human Monocytes", Cell Metabolism 19, Mar. 4, 2014, pp. 484-497.
Park et al., "Resistin in Rodents and Humans", Diabetes & Metabolism Journal, 37, 2013, pp. 404- 414.
Ouchi et al., "Adipokines in Inflammation and Metabolic Disease", Nature Reviews, Immunology, vol. 11, Feb. 2011, pp. 85-97.
Steppan et al., "The Hormone Resistin Links Obesity to Diabetes", Nature, vol. 409, Jan. 18, 2001, pp. 307-312.
Patel et al., "Disulfide-Dependent Multimeric Assembly of Resistin Family Hormones", Science, vol. 304, May 21, 2004, pp. 1154-1158.
Search Report and Written Opinion in International Application No. PCT/KR2017/011963, dated Jan. 30, 2018, 11 pages.
Chemical Abstract Compound, STN Express RN 1538585-64-6 (Entered STN: Feb. 6, 2014), 1 page.

* cited by examiner

*Primary Examiner* — Brenda L Coleman
(74) *Attorney, Agent, or Firm* — Marshall, Gerstein & Borun LLP

(57) ABSTRACT

The present invention relates to a compound represented by Chemical Formula 1, or a pharmaceutically acceptable salt thereof. The compound according to the present invention can be usefully used for the prevention or treatment of cardiovascular diseases.

7 Claims, No Drawings

3-AMINOALKYLATED INDOLE DERIVATIVE, METHOD FOR THE PREPARATION THEREOF, AND PHARMACEUTICAL COMPOSITION COMPRISING THE SAME

TECHNICAL FIELD

The present invention relates to a novel 3-aminoalkylated indole derivative which can be usefully used for the prevention or treatment of cardiovascular diseases, a method for the preparation thereof and a pharmaceutical composition comprising the same.

BACKGROUND OF ART

Recently, as adipokine, a hormone secreted by fat, is known to play an important role in the occurrence of obesity-related complications in addition to known hematologic and metabolic factors, it is expected to be able to prevent or treat related diseases by adjusting their actions.

The importance of adipokine has been proven that severe insulin resistance, hyperglycemia, hyperlipidemia, fatty liver and the like have been found in animal models or humans having a congenital deficiency of adipose tissue. Representative types of the adipokines which have been known to date include leptin, adiponectin, TNF-alpha, Resistin, interleukin-6, plasminogen activator inhibitor-1, TGF-beta and the like (Nat Rev Immunol, 2011, 11(2), 85-97). Resistin was first discovered as a substance that mediates insulin resistance in obese mice.

Rodent resistin is secreted from adipocytes, which is presumed to be associated with obesity-related insulin resistance and type 2 diabetes (Nature, 2001, 409, 307-312). However, human resistin is quite different from rodent resistin. Human resistin is a cytokine that is secreted from monocytes and induces chronic inflammations. These chronic inflammations can lead to diabetes, obesity, liver disease, arteriosclerosis, rheumatoid arthritis and other cardiovascular diseases (Diabetes Metab J, 2013, 37, 404-414).

Resistin is a small protein of 12.5 Kda, and six monomers are linked to each other to form a hexamer (Science 2004, 304, 1154-1158). In a recent research, it was first discovered in the world that the receptor for human resistin is CAP1. Resistin increases cAMP via CAP1 and induces the expression of inflammatory cytokines via PKA, NFkB signaling system. Further, the research has reported that human resistin directly binds to CAP1 in monocytes, and involves in cAMP concentration, PKA activity and NF-kappaB-related transcription of inflammatory cytokines, and over-expression of CAP1 enhanced resistin-induced increased activity of cAMP-dependent signaling pathway. In particular, the transgenic mouse model has been shown that CAP1-over-expressed monocytes aggravated adipose tissue inflammation in transgenic mice. In contrast, it has been shown that inhibition of CAP1 expression abrogated the resistin-mediated inflammatory activity both in vitro and in vivo (Cell Metab, 2014, 19(3), 484-497).

Therefore, by developing a drug that effectively adjusts the action of resistin and CAP1, it is expected to be able to prevent and treat related diseases, especially cardiovascular diseases.

DETAILED DESCRIPTION OF THE INVENTION

Technical Problem

It is one object of the present invention to provide a novel 3-aminoalkylated indole derivative which can be usefully used for the prevention or treatment of cardiovascular diseases, and a method for the preparation thereof.

It is another object of the present invention to provide a pharmaceutical composition comprising the 3-aminoalkylated indole derivative.

Technical Solution

In order to achieve the above objects, the present invention provides a compound represented by the following Chemical Formula 1, or a pharmaceutically acceptable salt thereof:

[Chemical Formula 1]

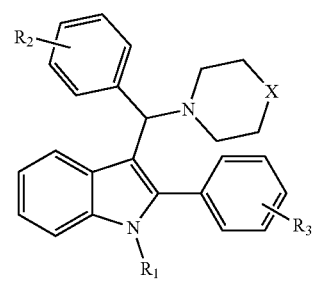

In Chemical Formula 1,
$R_1$ is hydrogen, or $C_{1-4}$ alkyl,
$R_2$ is hydrogen, $C_{1-4}$ alkyl, $C_{1-4}$ alkoxy, $C_{1-4}$ haloalkyl, or halogen,
$R_3$ is hydrogen, or halogen,
X is O, or N—$R_4$, and
$R_4$ is hydrogen, or $C_{1-4}$ alkyl.
Preferably, $R_1$ is hydrogen, or methyl.
Preferably, $R_2$ is hydrogen, methoxy, trifluoromethyl, fluoro, or chloro.
Preferably, $R_3$ is hydrogen, or chloro.
Preferably, $R_4$ is methyl, or ethyl.
Representative examples of the compound represented by Chemical Formula 1 are as follows:
1) 4-(phenyl(2-phenyl-1H-indol-3-yl)methyl)morpholine,
2) 3-((4-chlorophenyl)(4-methylpiperazin-1-yl)methyl)-2-phenyl-1H-indole,
3) 4-((3-fluorophenyl)(2-phenyl-1H-indol-3-yl)methyl)morpholine,
4) 4-((2-phenyl-1H-indol-3-yl)(4-(trifluoromethyl)phenyl)methyl)morpholine,
5) 4-((1-methyl-2-phenyl-1H-indol-3-yl)(phenyl)methyl)morpholine,
6) 3-((4-methylpiperazin-1-yl)(phenyl)methyl)-2-phenyl-1H-indole,
7) 3-((3-fluorophenyl)(4-methylpiperazin-1-yl)methyl)-2-phenyl-1H-indole,
8) 3-((4-methylpiperazin-1-yl)(4-(trifluoromethyl)phenyl)methyl)-2-phenyl-1H-indole,
9) 4-((4-fluorophenyl)(2-phenyl-1H-indol-3-yl)methyl)morpholine,
10) 3-((4-fluorophenyl)(4-methylpiperazin-1-yl)methyl)-2-phenyl-1H-indole,
11) 4-((4-chlorophenyl)(2-(4-chlorophenyl)-1H-indol-3-yl)methyl)morpholine,
12) 2-(4-chlorophenyl)-3-((4-chlorophenyl)(4-methylpiperazin-1-yl)methyl)-1H-indole,
13) 4-((2-(4-chlorophenyl)-1H-indol-3-yl)(3-fluorophenyl)methyl)morpholine,
14) 2-(4-chlorophenyl)-3-((3-fluorophenyl)(4-methylpiperazin-1-yl)methyl)-1H-indole, 15) 2-(4-chlorophenyl)-3-((4-fluorophenyl)(4-methylpiperazin-1-yl)methyl)-1H-indole,
16) 4-((2-(4-chlorophenyl)-1H-indol-3-yl)(4-(trifluoromethyl)phenyl)methyl)morpholine,
17) 2-(4-chlorophenyl)-3-((4-methylpiperazin-1-yl)(4-(trifluoromethyl)phenyl)methyl)-1H-indole,
18) 3-((4-ethylpiperazin-1-yl)(4-fluorophenyl)methyl)-2-phenyl-1H-indole,
19) 3-((4-ethylpiperazin-1-yl)(4-(trifluoromethyl)phenyl)methyl)-2-phenyl-1H-indole, and
20) 4-((3-methoxyphenyl)(2-phenyl-1H-indol-3-yl)methyl)morpholine.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compound.

As the free acid, an organic acid and an inorganic acid can be used. Examples of the inorganic acids include hydrochloric acid, phosphoric acid, sulfuric acid, nitric acid, tartaric acid and the like. Examples of the organic acids include methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycollic acid, gluconic acid, galacturonic acid, glutamic acid, glutaric acid, glucuronic acid, aspartic acid, ascorbic acid, carbonic acid, vanillic acid, hydroiodic acid and the like, but are not limited thereto.

In addition, a pharmaceutically acceptable metal salt can be obtained by a conventional method using a base. For example, a compound represented by Chemical Formula 1 is dissolved in an excessive amount of an alkali metal hydroxide or an alkaline earth metal hydroxide solution, the non-soluble salt is filtered, and the filtrate is evaporated and dried to obtain a pharmaceutically acceptable metal salt. At this time, it is particularly preferable to prepare a sodium salt, a potassium salt or a calcium salt as the metal salt.

A pharmaceutically unacceptable salt or solvate of the compound of Chemical Formula 1 may be used as an intermediate when preparing the compound of Chemical Formula 1, or the pharmaceutically acceptable salt or the solvate thereof.

Further, the compound of Chemical Formula 1 according to the present invention includes not only pharmaceutically acceptable salts thereof, but also solvates such as hydrates that can be prepared therefrom, and includes all possible stereoisomers, but are not limited thereto. The solvate and the stereoisomer of the compound of Chemical Formula 1 may be prepared from the compound of Chemical Formula 1 using common methods known in the art.

In addition, the compound of Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but also include a compound containing various amounts of water. The solvate of the compound of Chemical Formula 1 according to the present invention includes both stoichiometric solvates and non-stoichiometric solvates.

Furthermore, as an example, the present invention can produce the compound represented by Chemical Formula 1 through Reaction Scheme 1 below.

[Reaction Scheme 1]

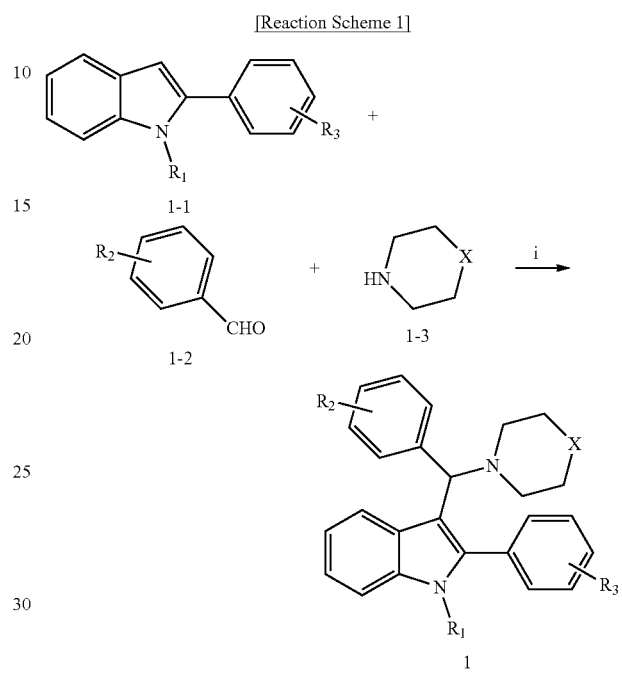

In Reaction Scheme 1, $R_1$ to $R_3$, and X are as previously defined.

The above reaction is carried out by reacting a compound represented by Chemical Formula 1-1, a compound represented by Chemical Formula 1-2, and a compound represented by Chemical Formula 1-3 to produce a compound represented by Chemical Formula 1.

The reaction is preferably carried out at 80° C. to 90° C. Further, it is desirable to use ethylene glycol as a solvent for the reaction.

Further, the present invention provides a pharmaceutical composition for preventing or treating cardiovascular diseases, comprising the compound represented by Chemical Formula 1, or a pharmaceutically acceptable salt, hydrate, solvate or isomer thereof as an active ingredient.

The compound according to the present invention can be used for preventing or treating cardiovascular diseases by inhibiting the binding of resistin and CAP1 and thereby inhibiting the expression of inflammatory cytokines. The cardiovascular disease includes arteriosclerosis, hypertension, angina pectoris, myocardial infarction, or stroke.

As used herein, the term "prevention" refers to any act to delay or inhibit occurrence, spread or recurrence of the above-mentioned diseases by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administered daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof can be usefully used for the prevention or treatment of cardiovascular diseases.

Detailed Description of the Embodiments

Below, the present invention will be described in more detail by way of examples. However, these examples are provided for illustrative purposes only, and should not be construed as limiting the scope of the present invention to these examples.

Example 1: Preparation of 4-(phenyl(2-phenyl-1H-indol-3-yl)methyl)morpholine

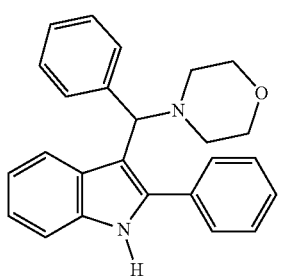 [SMILES: c1ccc(-c2[nH]c3ccccc3c2C(c2ccccc2)N2CCOCC2)cc1]

Benzaldehyde (0.03 mL, 0.30 mmol) and morpholine (0.03 mL, 0.38 mmol) were dissolved in ethylene glycol (0.25 mL). The mixture was stirred at room temperature for 10 to 30 minutes. Then, 2-phenyl-1H-indole (0.05 g, 0.25 mmol) was added thereto and stirred for 3 days while maintaining the internal temperature at 70° C. to 80° C., and the termination of the reaction was confirmed by TLC. The reaction solution was cooled to room temperature, water (10 mL) was added, and the mixture was extracted twice with ethyl acetate (10 mL). The organic layer was dried over $Na_2SO_4$ and concentrated under reduced pressure. The resulting residue was crystallized from ethyl acetate/n-hexane (1:1 to 1:5). The obtained solid was filtered to obtain the title compound (0.03 g, 29.0%).

MS m/z 368 [M]+; HRMS (+EI) calcd for $C_{25}H_{24}N_2O$ [M]+ 368.1889, found 368.1886.

1H NMR (500 MHz, MeOD): 8.23 (d, 1H), 7.53 (d, 2H), 7.49 (t, 2H), 7.42 (d, 3H), 7.31 (d, 1H), 7.18 (t, 2H), 7.10 (t, 2H), 7.03 (t, 1H), 4.68 (s, 1H), 3.68 (t, 4H), 2.46 (m, 2H), 2.38 (m, 2H)

Hereinafter, compounds of Examples 2 to 20 are produced in the same manner as in Example 1, except that reactants corresponding to the chemical structure of the compound to be produced were used.

Example 2: Preparation of 3-((4-chlorophenyl)(4-methylpiperazin-1-yl)methyl)-2-phenyl-1H-indole

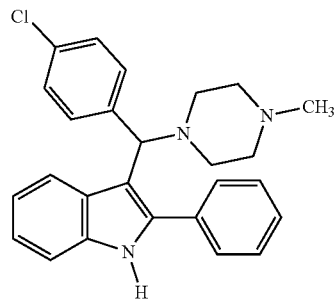 [SMILES: CN1CCN(C(c2ccc(Cl)cc2)c2c(-c3ccccc3)[nH]c3ccccc23)CC1]

MS m/z 415 [M]+; HRMS (+EI) calcd for $C_{26}H_{26}ClN_3$ [M]+ 415.1815, found 415.1814.

1H NMR (500 MHz, MeOD): 8.07 (d, 1H), 7.52 (m, 4H), 7.49 (d, 1H), 7.42 (d, 2H), 7.36 (d, 1H), 7.18 (d, 2H), 7.10 (t, 1H), 7.02 (t, 1H), 4.76 (s, 1H), 3.35 (m, 4H), 2.50 (br, 4H), 2.27 (s, 3H)

Example 3: Preparation of 4-((3-fluorophenyl)(2-phenyl-1H-indol-3-yl)methyl)morpholine

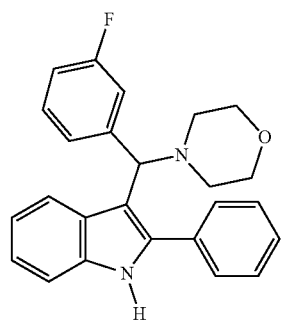 [SMILES: Fc1cccc(C(c2c(-c3ccccc3)[nH]c3ccccc23)N2CCOCC2)c1]

MS m/z 386 [M]+; HRMS (+EI) calcd for $C_{25}H_{23}FN_2O$ [M]+ 386.1794, found 386.1794.

1H NMR (500 MHz, MeOD): 8.14 (d, 1H), 7.50 (m, 4H), 7.44 (t, 1H), 7.32 (d, 1H), 7.16 (m, 3H), 7.11 (t, 1H), 7.04 (t, 1H), 6.82 (t, 1H), 4.72 (s, 1H), 3.71 (t, 4H), 2.50 (br, 2H), 2.41 (br, 2H)

Example 4: Preparation of 4-((2-phenyl-1H-indol-3-yl)(4-(trifluoromethyl)phenyl)methyl)morpholine

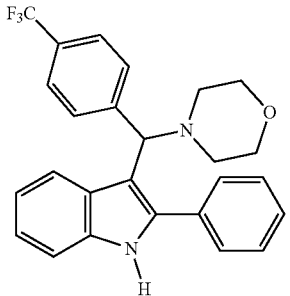 [SMILES: FC(F)(F)c1ccc(C(c2c(-c3ccccc3)[nH]c3ccccc23)N2CCOCC2)cc1]

MS m/z 436 [M]+; HRMS (+EI) calcd for $C_{26}H_{23}F_3N_2O$ [M]+ 436.1762, found 436.1761.

1H NMR (500 MHz, MeOD): 8.12 (d, 1H), 7.78 (d, 1H), 7.54 (m, 6H), 7.47 (m, 2H), 7.41 (d, 1H), 7.33 (t, 1H), 7.10 (t, 1H), 7.04 (t, 1H), 4.82 (s, 1H), 3.72 (t, 4H), 2.52 (br, 2H), 2.40 (br, 2H)

Example 5: Preparation of 4-((1-methyl-2-phenyl-1H-indol-3-yl)(phenyl)methyl)morpholine

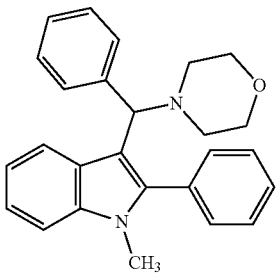 [SMILES: Cn1c(-c2ccccc2)c(C(c2ccccc2)N2CCOCC2)c2ccccc21]

MS m/z 382 [M]+; HRMS (+EI) calcd for $C_{26}H_{26}N_2O$ [M]+ 382.2045, found 382.2047.

1H NMR (500 MHz, MeOD): 8.23 (d, 1H), 7.54 (m, 3H), 7.32 (m, 5H), 7.18 (m, 3H), 7.09 (m, 2H), 4.34 (s, 1H), 3.68 (t, 4H), 2.41 (br, 2H), 2.35 (br, 2H)

Example 6: Preparation of 3-((4-methylpiperazin-1-yl)(phenyl)methyl)-2-phenyl-1H-indole

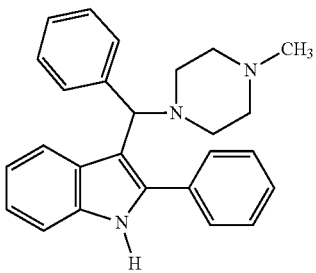 [SMILES: CN1CCN(C(c2ccccc2)c2c(-c3ccccc3)[nH]c3ccccc23)CC1]

MS m/z 381 [M]+; HRMS (+EI) calcd for $C_{26}H_{27}N_3$[M]+ 381.2205, found 381.2203.

1H NMR (500 MHz, MeOD): 8.17 (d, 1H), 7.53 (t, 2H), 7.48 (m, 3H), 7.42 (d, 3H), 7.31 (d, 1H), 7.17 (t, 2H), 7.10 (d, 2H), 7.02 (t, 1H), 4.72 (s, 1H), 3.30 (m, 4H), 2.47 (br, 4H), 2.27 (s, 3H)

Example 7: Preparation of 3-((3-fluorophenyl)(4-methylpiperazin-1-yl)methyl)-2-phenyl-1H-indole

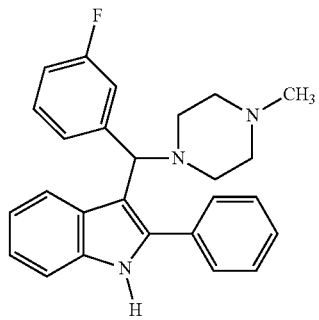 [SMILES: CN1CCN(C(c2cccc(F)c2)c2c(-c3ccccc3)[nH]c3ccccc23)CC1]

MS m/z 399 [M]+; HRMS (+EI) calcd for $C_{26}H_{26}FN_3$ [M]+ 399.2111, found 399.2109.

1H NMR (500 MHz, MeOD): 8.07 (d, 1H), 7.51 (m, 4H), 7.43 (t, 1H), 7.32 (d, 1H), 7.14 (m, 4H), 7.03 (t, 1H), 6.82 (t, 1H), 4.76 (s, 1H), 3.27 (m, 4H), 2.49 (br, 4H), 2.28 (s, 3H)

Example 8: Preparation of 3-((4-methylpiperazin-1-yl)(4-(trifluoromethyl)phenyl)methyl)-2-phenyl-1H-indole

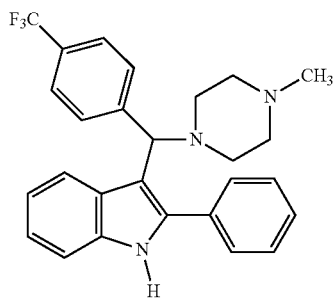 [SMILES: CN1CCN(C(c2ccc(C(F)(F)F)cc2)c2c(-c3ccccc3)[nH]c3ccccc23)CC1]

MS m/z 449 [M]+; HRMS (+EI) calcd for $C_{27}H_{26}F_3N_3$ [M]+ 449.2079, found 449.2076.

1H NMR (500 MHz, MeOD): 8.05 (d, 1H), 7.55 (m, 4H), 7.51 (d, 2H), 7.45 (m, 3H), 7.33 (d, 1H), 7.10 (t, 1H), 7.02 (t, 1H), 4.80 (s, 1H), 3.26 (m, 4H), 2.51 (br, 4H), 2.28 (s, 3H)

Example 9: Preparation of 4-((4-fluorophenyl)(2-phenyl-1H-indol-3-yl)methyl)morpholine

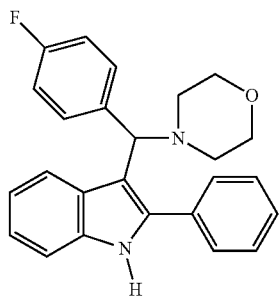 [SMILES: Fc1ccc(C(c2c(-c3ccccc3)[nH]c3ccccc23)N2CCOCC2)cc1]

MS m/z 386 [M]+; HRMS (+EI) calcd for $C_{25}H_{23}FN_2O$ [M]+ 386.1794, found 386.1793.

1H NMR (500 MHz, MeOD): 8.18 (d, 1H), 7.51 (m, 4H), 7.42 (t, 3H), 7.32 (d, 1H), 7.10 (t, 1H), 7.03 (t, 1H), 6.91 (t, 2H), 4.70 (s, 1H), 3.69 (t, 4H), 2.47 (m, 2H), 2.37 (m, 2H)

Example 10: Preparation of 3-((4-fluorophenyl)(4-methylpiperazin-1-yl)methyl)-2-phenyl-1H-indole

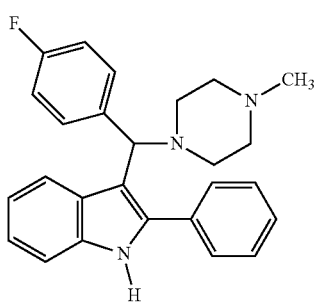 [SMILES: CN1CCN(C(c2ccc(F)cc2)c2c(-c3ccccc3)[nH]c3ccccc23)CC1]

MS m/z 399 [M]+; HRMS (+EI) calcd for $C_{26}H_{26}FN_3$ [M]+ 399.2111, found 399.2107.

1H NMR (500 MHz, MeOD): 8.11 (d, 1H), 7.50 (m, 4H), 7.40 (m, 3H), 7.31 (d, 1H), 7.09 (t, 1H), 7.02 (t, 1H), 6.90 (t, 2H), 3.74 (s, 1H), 3.36 (m, 4H), 2.49 (br, 4H), 2.27 (s, 3H)

Example 11: Preparation of 4-((4-chlorophenyl)(2-(4-chlorophenyl)-1H-indol-3-yl)methyl)morpholine

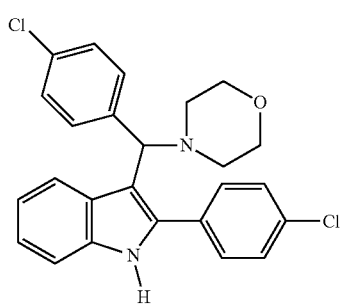 [SMILES: Clc1ccc(-c2[nH]c3ccccc3c2C(c2ccc(Cl)cc2)N2CCOCC2)cc1]

MS m/z 436 [M]+; HRMS (+EI) calcd for $C_{25}H_{22}Cl_2N_2O$ [M]+ 436.1109, found 436.1108.

1H NMR (500 MHz, MeOD): 8.16 (d, 1H), 7.51 (s, 4H), 7.38 (d, 2H), 7.32 (d, 1H), 7.18 (d, 2H), 7.12 (t, 1H), 7.05 (t, 1H), 4.68 (s, 1H), 3.69 (t, 4H), 2.47 (m, 2H), 2.37 (m, 2H)

Example 12: Preparation of 2-(4-chlorophenyl)-3-((4-chlorophenyl)(4-methylpiperazin-1-yl)methyl)-1H-indole

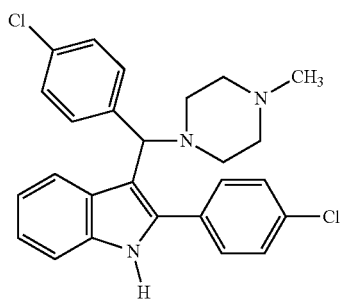 [SMILES: CN1CCN(C(c2ccc(Cl)cc2)c2c(-c3ccc(Cl)cc3)[nH]c3ccccc23)CC1]

MS m/z 449 [M]+; HRMS (+EI) calcd for $C_{26}H_{25}Cl_2N_3$ [M]+ 449.1426, found 449.1423.

1H NMR (500 MHz, MeOD): 8.09 (d, 1H), 7.51 (s, 4H), 7.37 (d, 2H), 7.32 (d, 1H), 7.17 (d, 2H), 7.11 (t, 1H), 7.03 (t, 1H), 4.71 (s, 1H), 3.34 (m, 4H), 2.49 (br, 4H), 2.28 (s, 3H)

Example 13: Preparation of 4-((2-(4-chlorophenyl)-1H-indol-3-yl)(3-fluorophenyl)methyl)morpholine

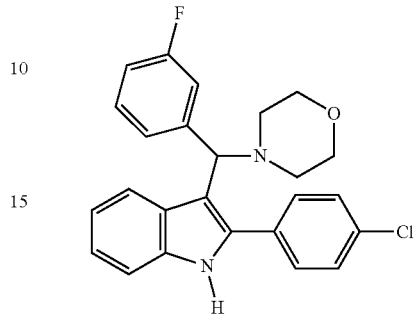

MS m/z 420 [M]+; HRMS (+EI) calcd for $C_{25}H_{22}ClFN_2O$ [M]+ 420.1405, found 420.1404.

1H NMR (500 MHz, MeOD): 8.16 (d, 1H), 7.52 (s, 4H), 7.32 (d, 1H), 7.17 (d, 2H), 7.12 (d, 2H), 7.06 (t, 1H), 6.83 (t, 1H), 4.70 (s, 1H), 3.70 (t, 4H), 2.49 (m, 2H), 2.41 (m, 2H)

Example 14: Preparation of 2-(4-chlorophenyl)-3-((3-fluorophenyl)(4-methylpiperazin-1-yl)methyl)-1H-indole

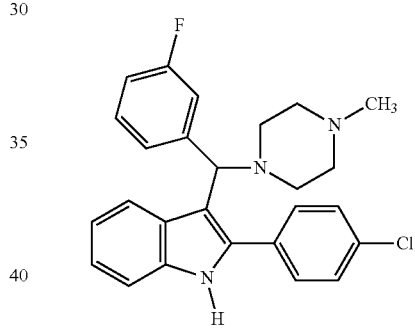

MS m/z 433 [M]+; HRMS (+EI) calcd for $C_{26}H_{25}ClFN_3$ [M]+ 433.1721, found 433.1721.

1H NMR (500 MHz, MeOD): 8.08 (d, 1H), 7.52 (s, 4H), 7.32 (d, 1H), 7.17 (d, 2H), 7.12 (m, 2H), 7.04 (t, 1H), 6.83 (t, 1H), 4.73 (s, 1H), 3.36 (m, 4H), 2.51 (br, 4H), 2.28 (d, 3H)

Example 15: Preparation of 2-(4-chlorophenyl)-3-((4-fluorophenyl)(4-methylpiperazin-1-yl)methyl)-1H-indole

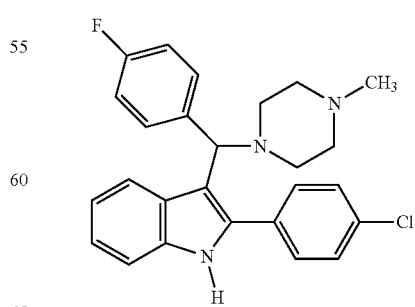

MS m/z 433 [M]+; HRMS (+EI) calcd for $C_{26}H_{25}ClFN_3$ [M]+ 433.1721, found 433.1721.

1H NMR (500 MHz, MeOD): 8.12 (d, 1H), 7.50 (m, 4H), 7.41 (t, 2H), 7.32 (d, 1H), 7.11 (t, 1H), 7.04 (t, 1H), 6.91 (m, 2H), 4.70 (s, 1H), 3.37 (m, 4H), 2.48 (br, 4H), 2.27 (s, 3H)

Example 16: Preparation of 4-((2-(4-chlorophenyl)-1H-indol-3-yl)(4-(trifluoromethyl)phenyl)methyl)morpholine

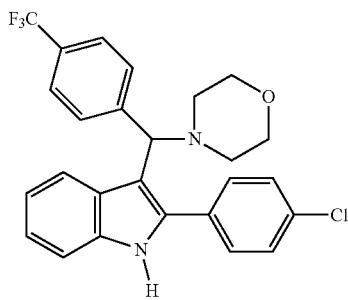 [SMILES: FC(F)(F)c1ccc(C(c2c(-c3ccc(Cl)cc3)[nH]c3ccccc23)N2CCOCC2)cc1]

MS m/z 470 [M]+; HRMS (+EI) calcd for C₂₆H₂₂ClF₃N₂O [M]+ 470.1373, found 433.1376.
1H NMR (500 MHz, MeOD): 8.13 (d, 1H), 7.57 (d, 2H), 7.51 (s, 4H), 7.42 (d, 2H), 7.34 (d, 1H), 7.12 (t, 1H), 7.05 (t, 1H), 4.80 (s, 1H), 3.73 (m, 4H), 2.59 (m, 2H), 2.40 (m, 2H)

Example 17: Preparation of 2-(4-chlorophenyl)-3-((4-methylpiperazin-1-yl)(4-(trifluoromethyl)phenyl)methyl)-1H-indole

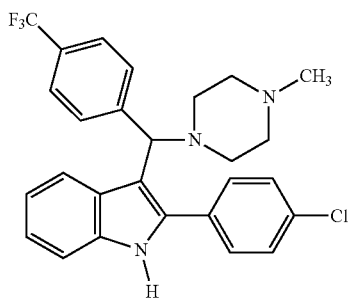 [SMILES: CN1CCN(C(c2ccc(C(F)(F)F)cc2)c2c(-c3ccc(Cl)cc3)[nH]c3ccccc23)CC1]

MS m/z 483 [M]+; HRMS (+EI) calcd for C₂₇H₂₅ClF₃N₃ [M]+ 483.1869, found 483.1869.
1H NMR (500 MHz, MeOD): 8.08 (d, 1H), 7.56 (d, 2H), 7.52 (s, 4H), 7.47 (d, 2H), 7.33 (d, 1H), 7.12 (t, 1H), 7.04 (t, 1H), 4.58 (s, 1H), 3.27 (m, 4H), 2.60 (br, 4H), 2.34 (s, 3H)

Example 18: Preparation of 3-((4-ethylpiperazin-1-yl)(4-fluorophenyl)methyl)-2-phenyl-1H-indole

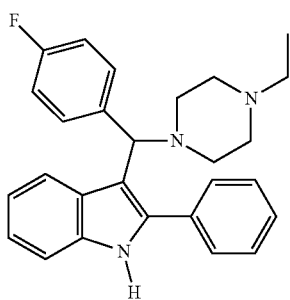 [SMILES: CCN1CCN(C(c2ccc(F)cc2)c2c(-c3ccccc3)[nH]c3ccccc23)CC1]

MS m/z 413 [M]+; HRMS (+EI) calcd for C₂₇H₂₈FN₃ [M]+ 413.2267, found 413.2267.

1H NMR (500 MHz, MeOD): 8.08 (d, 1H), 7.51 (m, 4H), 7.44 (m, 3H), 7.33 (d, 1H), 7.11 (t, 1H), 7.03 (t, 1H), 6.94 (t, 2H), 4.79 (s, 1H), 3.35 (m, 4H), 2.87 (br, 4H), 2.77 (q, 2H), 1.18 (t, 3H)

Example 19: Preparation of 3-((4-ethylpiperazin-1-yl)(4-(trifluoromethyl)phenyl)methyl)-2-phenyl-1H-indole

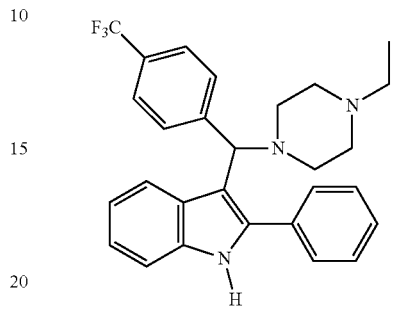

1H NMR (500 MHz, MeOD): 8.05 (d, 1H), 7.54 (m, 4H), 7.50 (t, 2H), 7.45 (t, 3H), 7.31 (d, 1H), 7.09 (t, 1H), 7.02 (t, 1H), 4.89 (s, 1H), 3.34 (m, 4H), 2.46 (br, 4H), 2.44 (q, 2H), 1.08 (t, 3H)

Example 20: Preparation of 4-((3-methoxyphenyl)(2-phenyl-1H-indol-3-yl)methyl)morpholine

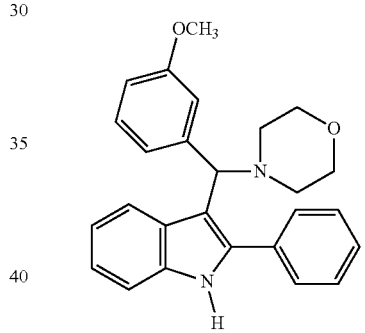

MS m/z 398 [M]+; HRMS (+EI) calcd for C₂₆H₂₆N₂O₂ [M]+ 398.1994, found 398.1996.
1H NMR (500 MHz, MeOD): 8.25 (d, 1H), 7.54 (d, 2H), 7.50 (t, 2H), 7.42 (t, 1H), 7.31 (d, 1H), 7.09 (m, 2H), 7.02 (m, 2H), 6.96 (d, 1H), 6.66 (d, 1H), 4.65 (s, 1H), 3.69 (t, 4H), 3.64 (s, 3H), 2.47 (m, 2H), 2.40 (m, 2H)

Experimental Example: Evaluation of the Ability to Inhibit TNF-α Secretion by hResistin Using THP-1 (human monocyte) cell line and ELISA system, the abilities to inhibit TNF-α secretion by hResistin (IC₅₀) were evaluated for the compounds prepared in the above examples. The compounds target hResistin, and the abilities of the compounds to inhibit TNF-α secretion by human recombinant Resistin in human monocyte (THP-1) were evaluated. The abilities to inhibit TNF-α secretion were assessed by ELISA quantifying the amount of antibody with the enzyme as a marker using an antigen-antibody reaction.

Specifically, the cultured cells were spun down at 1,500 rpm for 2 minutes, the supernatant was removed and then the cells were re-suspended in 10 mL of complete RPMI-1640 medium. After counting the number of cells using Luna™ Automated Cell Counter, cells were plated into 96-well assay plates at 50 μL per well. The cells cultured for 24 hours were treated with the test substances in accordance with the concentration for 1 hour, and then the supernatant was collected and subjected to ELISA assay. In the ELISA assay, the absorbance at 450 nm ($OD_{450\ nm}$) was measured using Flexstation 3. The ability of each test substance to inhibit TNF-α secretion ($IC_{50}$) and its inhibition at a concentration of 5 uM are shown in Table 1 below.

TABLE 1

| Examples No. | $IC_{50}$(uM) | Inhibition (5 uM, %) |
|---|---|---|
| 2 | 4.4 | 70.3 |
| 6 | 2.8 | |
| 7 | 2 | |
| 8 | 1 | |
| 9 | 3.5 | |
| 10 | 1.7 | |
| 12 | 0.4 | |
| 14 | 3.2 | |
| 15 | 1.5 | |
| 18 | 1.7 | |
| 19 | 1.7 | |

What is claimed is:

1. A compound represented by the following Chemical Formula 1, or a pharmaceutically acceptable salt thereof:

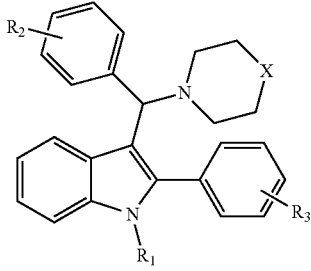

[Chemical Formula 1]

in Chemical Formula 1,
$R_1$ is hydrogen, or $C_{1-4}$ alkyl,
$R_2$ is hydrogen, $C_{1-4}$ alkyl, $C_{1-4}$ alkoxy, $C_{1-4}$ haloalkyl, or halogen,
$R_3$ is hydrogen, or halogen,
X is N—$R_4$, and
$R_4$ is hydrogen, or $C_{1-4}$ alkyl.

2. The compound or a pharmaceutically acceptable salt thereof according to claim 1, wherein $R_1$ is hydrogen, or methyl.

3. The compound or a pharmaceutically acceptable salt thereof according to claim 1, wherein $R_2$ is hydrogen, methoxy, trifluoromethyl, fluoro, or chloro.

4. The compound or a pharmaceutically acceptable salt thereof according to claim 1, wherein $R_3$ is hydrogen, or chloro.

5. The compound or a pharmaceutically acceptable salt thereof according to claim 1, wherein $R_4$ is methyl or ethyl.

6. The compound or a pharmaceutically acceptable salt thereof according to claim 1, wherein the compound represented by the formula 1 is any one selected from the group consisting of:
 (1) 3-((4-chlorophenyl)(4-methylpiperazin-1-yl)methyl)-2-phenyl-1H-indole,
 (2) 3-((4-methylpiperazin-1-yl)(phenyl)methyl)-2-phenyl-1H-indole,
 (3) 3-((3-fluorophenyl)(4-methylpiperazin-1-yl)methyl)-2-phenyl-1H-indole,
 (4) 3-((4-methylpiperazin-1-yl)(4-(trifluoromethyl)phenyl)methyl)-2-phenyl-1H-indole,
 (5) 3-((4-fluorophenyl)(4-methylpiperazin-1-yl)methyl)-2-phenyl-1H-indole,
 (6) 2-(4-chlorophenyl)-3-((4-chlorophenyl)(4-methylpiperazin-1-yl)methyl)-1H-indole,
 (7) 2-(4-chlorophenyl)-3-((3-fluorophenyl)(4-methylpiperazin-1-yl)methyl)-1H-indole,
 (8) (2-(4-chlorophenyl)-3-((4-fluorophenyl)(4-methylpiperazin-1-yl)methyl)-1H-indole,
 (9) 2-(4-chlorophenyl)-3-((4-methylpiperazin-1-yl)(4-(trifluoromethyl)phenyl)methyl)-1H-indole,
 (10) 3-((4-ethylpiperazin-1-yl)(4-fluorophenyl)methyl)-2-phenyl-1H-indole, and
 (11) 3-((4-ethylpiperazin-1-yl)(4-(trifluoromethyl)phenyl)methyl)-2-phenyl-1H-indole.

7. A pharmaceutical composition for treating cardiovascular diseases, comprising the compound according to claim 1 or a pharmaceutically acceptable salt thereof.

* * * * *